(12) United States Patent
Luria

(10) Patent No.: US 8,158,740 B2
(45) Date of Patent: *Apr. 17, 2012

(54) HYDROPHILIC SILICONES

(75) Inventor: Leonard William Luria, Tampa, FL (US)

(73) Assignee: One Unlimited, Inc., Tampa, FL (US)

( * ) Notice: Subject to any disclaimer, the term of this patent is extended or adjusted under 35 U.S.C. 154(b) by 136 days.

This patent is subject to a terminal disclaimer.

(21) Appl. No.: 12/701,312

(22) Filed: Feb. 5, 2010

(65) Prior Publication Data

US 2010/0137546 A1  Jun. 3, 2010

Related U.S. Application Data

(63) Continuation-in-part of application No. 11/542,996, filed on Oct. 4, 2006, now Pat. No. 7,687,592.

(51) Int. Cl.
 *C08G 77/06* (2006.01)
 *C08F 6/04* (2006.01)

(52) U.S. Cl. ............ 528/29; 528/499; 528/502 A

(58) Field of Classification Search .............. None
 See application file for complete search history.

(56) References Cited

U.S. PATENT DOCUMENTS

| | | | |
|---|---|---|---|
| 3,133,111 A | 5/1964 | Wheeler et al. | |
| 3,600,418 A | 8/1971 | Bailey et al. | |
| 4,172,186 A | 10/1979 | Scott et al. | |
| 4,431,789 A | 2/1984 | Okazaki et al. | |
| 4,487,809 A | 12/1984 | Koerner et al. | |
| 5,073,195 A | 12/1991 | Cuthbert | |
| 5,144,054 A | 9/1992 | Shioya et al. | |
| 5,208,360 A | 5/1993 | Ward et al. | |
| 5,871,558 A | 2/1999 | Takei | |
| 6,251,981 B1 | 6/2001 | Tanaka et al. | |
| 6,258,969 B1 | 7/2001 | Sawai et al. | |
| 6,790,451 B2 | 9/2004 | Nakanishi | |
| 7,687,592 B2 * | 3/2010 | Runnels et al. ............ 528/29 |
| 2004/0146472 A1 | 7/2004 | Nakanishi | |
| 2004/0236003 A1 | 11/2004 | Del Torto et al. | |
| 2005/0033002 A1 | 2/2005 | Kishan | |
| 2005/0202257 A1 | 9/2005 | Gerritsen et al. | |
| 2007/0049716 A1 | 3/2007 | Sayre | |

FOREIGN PATENT DOCUMENTS

GB  875 109  8/1961

OTHER PUBLICATIONS

Jayakannan et al., Preparation of polyethers via proton acid catalyzed transetherification reactions, Macromol, Chem. Phys., 2000, pp. 759-767, 201, No. 7, India.

Pratt, et al., Reaction Rates by Distillation, The Etherification of Phenylcarbinols . . . , Dept. of Chemistry, Univ. of MD., 1949, pp. 2846-2849, vol. 71.

* cited by examiner

*Primary Examiner* — Marc Zimmer

(74) *Attorney, Agent, or Firm* — Saliwanchik, Lloyd & Eisenschenk

(57) ABSTRACT

A process for producing a soluble silicone product is provided. The process includes the steps of chemically reacting a polydialkoxysiloxane with an aliphatic alcohol with or without a catalyst in a reaction mixture, removing produced alcohol from the mixture; recovering the water soluble portion of produced silicone product, purifying the water soluble portion; and recovering hydrophilic material in the water insoluble portion.

15 Claims, No Drawings

HYDROPHILIC SILICONES

This is a continuation-in-part of U.S. patent application Ser. No. 11/542,996 filed Oct. 4, 2006 U.S. Pat. No. 7,687,592.

BACKGROUND OF THE INVENTION

Liquid silicone polymers, such as polydimethoxylsiloxane, have a very low solubility in water or aqueous solutions. In order to accommodate this property, they can be emulsified with the aid of surfactants in order to form aqueous emulsions, possibly stable for long periods or even indefinitely. Such emulsions consist of a suspension of very small droplets of liquid silicone, perhaps visible microscopically, but more easily characterized and monitored by light scattering. Despite the inherent instability of most emulsions, many cosmetics products are successfully based on emulsification. This has resulted from extensive experimentation in selecting the optimal surfactant and in confirming the emulsion stability of the product over an appropriate time period.

In order to provide water soluble silicones, there have also been prior art methods to chemically modify the silicone structure to circumvent the need for emulsification. These include dimethicone polyols (Siltech), cyclomethicones (Clearco) and polyesters (Zenitech). In contrast to the inventive goals, the reaction between alcohols and alkoxysiloxanes has been used to introduce hydrophobic properties; wood contains hydroxyl groups and, as a finely divided flour, has been reacted with oligoethoxysilioxanes to produce a solid material with low water affinity and compatibility with hydrocarbon polymers.

SUMMARY OF THE INVENTION

In accordance with the invention, a chemically modified silicone structure that is hydrophilic or water soluble to the extent needed for a particular application is provided.

This invention relates to the chemical modification of polyalkoxy siloxanes, by reaction with alcohols and to useful applications of the products. This reaction with alcohols makes it feasible to produce numerous polysiloxanes with new properties and to customize the chemical structures for specific applications. In particular, the invention focuses on "hydrophilic silicones," i.e., polysiloxanes substituted with hydrophilic groups, for imparting hydrophilic properties, or if the degree of substitution is sufficient, resulting in water solubility.

More particularly, there is disclosed a process to produce a silicone compound that is modified by a reaction with an alcohol such as glycerol, a component used in cosmetics for many years and known for its soothing and softening of skin texture and for the lack of side reactions. The formation of this type of water soluble silicone is achieved by the chemical reaction between aliphatic alcohols and alkoxy groups on the silicon. Specifically, the invention uses the reaction between polydimethoxysiloxane and glycerol, as follows:

Equation (1)

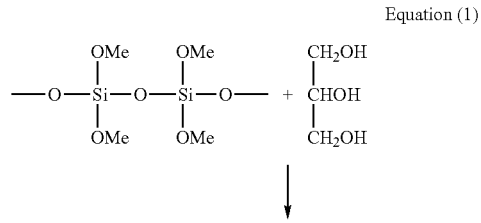

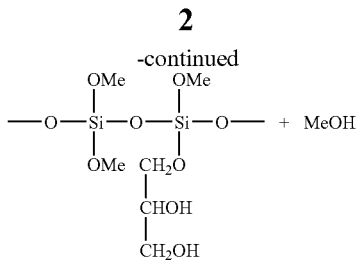

The mechanism of this reaction involves a nucleophilic attack on the silicon atom by the oxygen of a terminal hydroxyl group of the glycerol in order to form the —CH$_2$—O—Si— linkage. This linkage is then protected to some extent against hydrolysis by the presence of the glycerol moiety.

The inventive reaction may be subject to catalysis by acids and/or bases and may also require heating in order to attain reasonable reaction rates. The reaction can be driven to completion by removal of the methanol that is formed as the reaction proceeds. This can be accomplished by bubbling air or nitrogen through the reaction mixture.

The structural similarity between the reactants and products of the inventive reaction suggests that the changes in free energy are small and that the position of equilibrium can be easily manipulated.

Importantly, complete removal of produced methanol is required because of both the influence of residual methanol on yield and the toxicity of methanol itself. Consideration of these factors suggests that methoxy silicones are not necessarily preferred as the starting materials for products that are intended for human use. Instead, if only ethoxy substituents are used, any hydrolysis produces only ethanol, which is of very low toxicity. While it is unlikely that appreciable hydrolysis occurs either in storage or on the skin, if only ethoxy groups are present, slight hydrolysis thus becomes much less important.

In accordance with the invention, a similar reaction with 2-bromo-2-nitropropane-1,3-diol (sold commercially as Bronopol), which also has primary alcoholic hydroxyl groups, is possible with alkoxysiloxanes.

Equation (2)

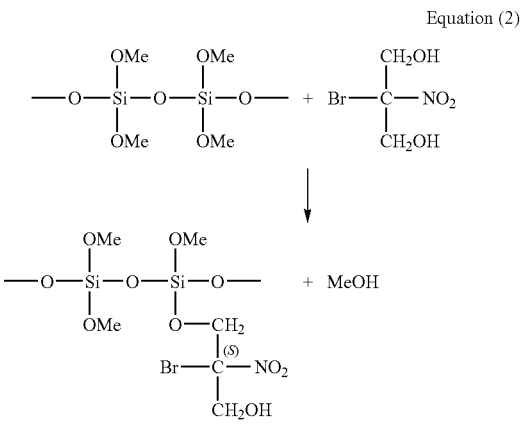

The use of the above reaction results in making both the antibacterial action and the water solubility of Bronopol an integral part of the resulting silicone molecules.

The modified silicones of the invention, when used in cosmetics, require no emulsification and should be stable in solution for long periods of time.

It is thus an object of the invention to produce silicones with hydrophilic properties varying from slight water adsorption to the extreme of water solubility.

Another object of the invention is to produce silicone polymers that are rendered water soluble without the need for emulsification.

A further object of the invention is to produce hydrophilic silicones by reacting a silicone compound with an alcohol.

Still another object of the invention is to produce a hydrophilic silicone by reacting a polysiloxane with an alcohol.

Still other objects and advantages of the invention will be made obvious from the following description.

DETAILED DESCRIPTION OF THE INVENTION

A method of preparing a water soluble silicone is provided. The method comprises the reaction between a polydialkoxysiloxane (the alkoxy usually being either methoxy or ethoxy) and an alcohol, such as glycerol, Bronopol, or mixtures of glycerol and Bronopol. In the inventive process, the alkoxy group of the silicone undergoes a reaction with an aliphatic hydroxyl group of the alcohol in order to form an —Si—O—CH$_2$— configuration with the alkoxy group of the alcohol. This reaction has been referred to in the past as "transetherification."

To carry out this reaction, the polydialkoxysiloxane is mixed with the alcohol, with or without the addition of a catalyst. Progress of the reaction is monitored by sampling the reaction mixture and testing for the appearance of water-soluble material. If the reaction velocity is inconveniently low, it may be increased by heating the reaction mixture. When a satisfactory amount of water-soluble material has been produced and recovered, the catalyst, if any, is removed or neutralized and the water-soluble fraction of the reaction mixture is purified, preferably by means of chromatography.

What has been discovered is that certain alcohols react under mild conditions with alkoxy groups situated on a polysiloxane chain in order to undergo what could be termed an "exchange reaction" or a "transetherification"; for example, the methoxy or ethoxy groups of the polyalkoxysiloxane are lost as methanol or ethanol while the alkoxy moiety of the reacting alcohol (usually of higher boiling point than that of methanol or ethanol) is bound to the polysiloxane. The inventive reaction thus provides a simple and rapid methodology for the modification of the chemical and physical properties of "silicones" having alkoxy groups in order to produce new chemical structures suitable for numerous applications.

The reaction with alkoxy groups requires a free alcohol group which has been in the past a primary, aliphatic group. It seems likely that reaction can be obtained also with secondary or tertiary groups, or with phenols, but probably with greatly decreased rates. The chemical reaction involved can be represented by the following equation:

Equation 3

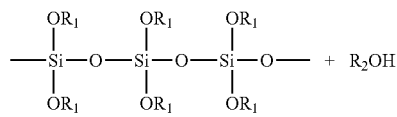

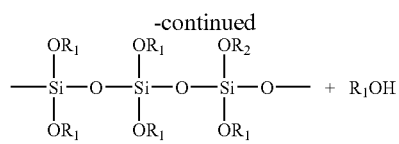

In theory, the above reaction is probably readily reversed so that, in a closed system, equilibrium would likely be reached in which all the species indicated would be present at concentrations not drastically different from each other. However, if the reactive groups on the silicone are methoxy or ethoxy, while R$_2$ is somewhat larger, the above reaction will easily go to completion by allowing the more volatile product to escape. In the present invention, two alcohols (R$_2$OH), namely, glycerol and Bronopol are preferred, but other alcohols can be used for the inventive reactions without departing from the scope of the invention.

Modifying silicones in accordance with the invention produces materials that are suitable as bases for numerous dermatological preparations, both human and veterinary. In addition, possible uses may be found as materials of construction, paints and coatings for home, agricultural and industrial products where some affinity for water is desirable. The inventive material is both water soluble and compatible with human skin, where it is able to form an extremely thin film on it. This film resists washing with water and imparts a feeling of softness, while protecting the skin from bacterial and fungal invasion by virtue of added protective agents.

The inventive reaction is carried out on a practical scale by mixing the alkoxypolysiloxane, usually methoxy or ethoxy, with the alcohol to be coupled to the silicone and then heating at between about 140°-300° F.

It has been discovered that the reaction time can be controlled via the modulation of temperature. It is noted that efficiency of removal of the alcohol during the reaction can influence the length of reaction time; the more efficient one is in removing the alcohol, the less the time period is for the reaction to reach maximum equilibrium.

More specifically, at a lower temperature range of between about 140° F. and 190° F., the heating period that is necessary for the reaction to go to completion (to reach maximum equilibrium) is far greater than 20 hours, and can in fact last up to several days. At between about 195° F. and 205° F., reaction time (to reach maximum equilibrium) is between about 20 and 22 hours, which represents the optimum reaction time for obtaining the desired result. By increasing the temperature to reach between about 210° F. and 220° F., reaction time (to reach maximum equilibrium) is reduced to between about 12 and 18 hours. At an even higher temperature of between about 225° F. and 235° F., the reaction time (to go to completion—to reach maximum equilibrium) is dramatically reduced to between about 5 and 8 hours. This significant time savings will allow the manufacturing process to be contained within a single 8 hour shift, thereby reducing the overall cost of the process, and eliminating additional variables that could affect the resulting end product. When the temperature is increased to greater than 250° F., reaction time will be decreased even further, however, the quality of the reaction and therefore the end product will be impacted. Verification performed by Mass-Spectrometry identified that the alcohol had bound to the siloxanes in all instances.

The addition of an acidic catalyst, such as hydrochloric acid or trichloroacetic acid, or a basic catalyst, such as N-ethyldisopropylamine or triethylamine, to the reaction may be found useful in achieving desired reaction rates. If the substituting alcohol has, in addition to the hydroxyl group consumed in the coupling reaction, additional hydrophilic groups, the polysiloxane product may be water soluble.

After the reaction mixture is heated and then cooled to room temperature, the water soluble portion can be obtained by mixing with water and recovering the water soluble portion by centrifugation, decantation or filtration. The residue left after the extraction with water may be expected to contain polysiloxane species that have reacted with too few alcohol molecules to give water solubility but, nevertheless, with a sufficient number to become very hydrophilic. Such material can be incorporated into dermatological salves and creams or other products where some wettability is desirable.

The water soluble material produced by the inventive process is then preferably fractionated, either by size exclusion chromatography (SEC) or high performance liquid chromatography (HPLC). Fractionation by HPLC serves to separate reaction products into many categories with slightly varying properties. This would reflect the enormous number of ways in which the polysiloxane structure may be substituted, both with respect to the degree of substitution and with respect to the arrangement of substituent groups along the polysiloxane chain.

Silicones substituted with glycerol or Bronopol, or combinations of the two, can be quite water soluble and, when applied in aqueous solution to the skin, leave a very thin film on the skin. They can impart also a hydrophobicity and an exceptionally smooth texture, which remains despite repeated exposures to water. The water solubility of such modified silicones strongly suggests that hydrophobic interactions between the polysiloxane and the skin are taking place. The modified silicones of the invention may promote healing in burn cases, both in terms of accelerating the healing process and in moderating pain.

The inventive silicone products could also be used as additions to finishes for many manufactured products since such additions discourage the accumulation of dust or other airborne contaminants. They are also potentially useful as a special class of lubricants since they could be attached covalently to surfaces using the reaction described in the equations set forth above, provided that the surface to be treated has free alcoholic —OH groups to act as an anchor for the polysiloxane.

Experimental results showing the feasibility for the synthesis of hydrophilic silicones by reacting polyalkoxysiloxones with aliphatic alcohols are given in Tables 1-3 below along with a brief indication of some of the properties of these products:

TABLE 1

| Example | Silicone substituents | Amt Silicone | Amt Glycerol | Amt Bronopol | Hrs. @ 200° F. | Result |
| --- | --- | --- | --- | --- | --- | --- |
| 214-112-7 | -0 Me | 5 ml | 2 ml | 3 g | 20 | Transparent gel indicating extensive reaction. |
| 214-112-8 | -0 Et | 5 ml | 2 ml | 3 g | 20 | Very little reaction as judged visually. Small amt. gel; most liquid silicone left. |
| 214-113-8 | -0 Et | 5 ml | 2 ml | 3 g | 60 | Extensive reaction. Stiff transparent gel. Skin test: judged better than Example 214-112-7 |
| 214-116-9 | -0 Me | 5 ml | 0.5 ml | 0.5 g | 20 | Clear colorless liquid; 2 mm solid gel on bottom of vial. Added 15 ml $H_2O$ & mixed --> turbid susp. little foaming; 8 da later→ gel. |
| 214-116-10 | -0 Et | 5 ml | 0.5 ml | 0.5 g | 20 | Clear slightly amber liquid with foaming; transparent solid on bottom. Added 15 ml $H_2O$ & mixed --> turbid suspension (much foaming). 8 days later: had formed clear liquid - no gel. |

TABLE 2

| Example | Silicone substituents | Amt Silicone | Amt Glycerol | Amount Bronopol | Hrs. @ 200° F. | Result |
| --- | --- | --- | --- | --- | --- | --- |
| 214-116-11 | —OMe | 5 ml | 0.2 ml | 0.1 g | 20 | Clear colorless liquid with solid transparent layer on bottom. 15 ml |

TABLE 2-continued

| Example | Silicone substituents | Amt Silicone | Amt Glycerol | Amount Bronopol | Hrs. @ 200° F. | Result |
|---|---|---|---|---|---|---|
| 214-116-12 | —OEt | 5 ml | 0.2 ml | 0.1 g | 20 | H$_2$O added & mixed - turbid suspension --> no foam. 8 days later: had formed stiff gel throughout. Clear, pale amber liquid with small translucent deposit on bottom. 15 ml H$_2$O added & shaken-→foam. 8 days later: clear liquid, no gel. |
| 214-133-Sup. 1 | —OEt | 20 ml | 0 | 2.0 g | 20 | H$_2$O extraction→ 75 ml ext., 3.8 g dry wt. Excellent cosmetic appeal. |

TABLE 3

| Example | Silicone substituents | Amt Silicone | Amt Glycerol | Amt Bronopol | Hrs @ x ° F. | Result |
|---|---|---|---|---|---|---|
| 215-281 | —OEt | 64.25 g | 38.5 g | | 20 Hr 200° F. | 2 layers - lower layer water soluble clear liquid - upper layer viscous liquid stable in water over 14 months |
| L1-40-09 | —OEt | 100 ml | 59.15 g | | 7.5 Hr 230° F. | 2 layers - lower layer water soluble clear liquid at 1% to 20% dilution in water - upper layer clear liquid slightly hydrophilic |
| 216-71-4 | —OMe | 5 ml | | 0.1 g | 17.5 Hr 215° F. | Clear to cloudy viscous liquid - NMR demonstrated strong reaction |

It will thus be seen that the objects set forth above, among those made apparent by the description, are attained by the inventive reaction and the silicone products produced thereby.

The inventive scope is now defined in the following claims.

The invention claimed is:

1. A method for producing a water soluble silicone, comprising:

reacting a mixture of poly(dialkoxy)siloxane having the structure

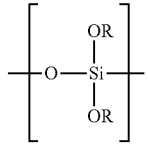

where R is methyl or ethyl and with an aliphatic alcohol selected from glycerol and 2-bromo-2-nitropropane-1,3-diol for a period of time and at a temperature sufficient to form one or more products comprising the structure:

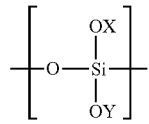

wherein X is

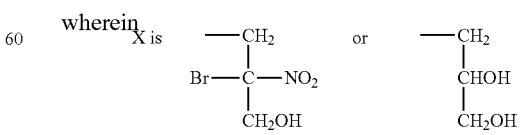

and

Y is —CH$_3$, —CH$_2$CH$_3$, or —X;

adding water to the one or more products; and isolating at least one hydrophilic silicone product.

2. The method of claim 1 wherein the isolating is by centrifugation, decantation or filtration.

3. The method of claim 1 wherein the heating is at a temperature between about 210° F. and about 235° F.

4. The method of claim 1 wherein the heating is at a temperature between about 225° F. and about 235° F.

5. The method of claim 1 wherein the time is between about 5 and about 18 hours.

6. The method of claim 1 wherein the time is between about 5 and about 8 hours.

7. The method of claim 1 further comprising addition of a catalytic amount of hydrochloric acid or trichloroacetic acid.

8. The method of claim 1 further comprising addition of a basic catalyst selected from the group consisting of N-ethyl-diisopropylamine and triethylamine.

9. A method of producing a water insoluble silicone material comprising:

reacting a polydialkoxysiloxane having the structure

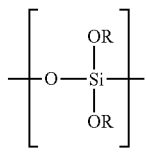

where R is methyl or ethyl with glycerol or 2-bromo-2-nitropropane 1,3-diol at a temperature between about 225° F. and about 235° F. for about 5 to about 8 hours;

extracting water soluble material from the reaction mixture; and fractionating water insoluble residue to obtain at least one insoluble silicone product characterized as having incomplete transetherification of the dialkoxy group of the siloxane with the glycerol or 2-bromo-2-nitropropane 1,3-diol.

10. The method of claim 1 or claim 9 further comprising removing ethanol or methanol formed in the reaction by bubbling air or nitrogen through the reaction mixture.

11. A water soluble silicone product having the structure

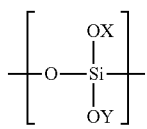

where

X is 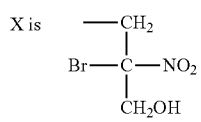

and

Y is —$CH_3$, —$CH_2CH_3$, or —X, prepared by the method of claim 1.

12. The water soluble silicone product of claim 11 which has the structure:

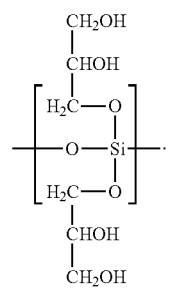

13. The water soluble silicone product of claim 11 which has the structure:

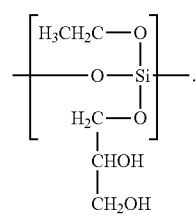

14. The water soluble silicone product of claim 11 which has the structure:

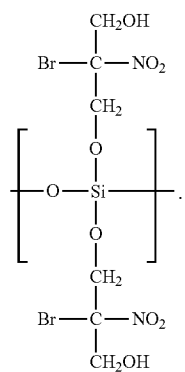

15. The water soluble silicone product of claim 11 which has the structure:

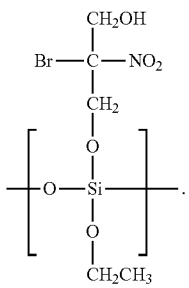

* * * * *

UNITED STATES PATENT AND TRADEMARK OFFICE
Certificate

Patent No. 8,158,740 B2                                                                                      Patented: April 17, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Leonard William Luria, Tampa, FL (US); Walter B. Dandliker (deceased), La Jolla, CA (US); and June K. Dandliker, (legal representative), La Jolla, CA (US).

Signed and Sealed this Twenty-fifth Day of December 2012.

*JAMES J. SEIDLECK*
*Supervisory Patent Examiner*
Art Unit 1765
Technology Center 1700